US006825357B2

(12) United States Patent
Rauchschwalbe et al.

(10) Patent No.: US 6,825,357 B2
(45) Date of Patent: Nov. 30, 2004

(54) BENZODIOXINOTHIOPHENES, THEIR PREPARATION AND USE

(75) Inventors: Günter Rauchschwalbe, Leverkusen (DE); Alexander Klausener, Pulheim (DE); Stephan Kirchmeyer, Leverkusen (DE); Knud Reuter, Krefeld (DE)

(73) Assignee: Bayer Aktiengesellschaft, Leverkusen (DE)

( * ) Notice: Subject to any disclaimer, the term of this patent is extended or adjusted under 35 U.S.C. 154(b) by 248 days.

(21) Appl. No.: 10/191,647

(22) Filed: Jul. 9, 2002

(65) Prior Publication Data

US 2003/0028024 A1 Feb. 6, 2003

(30) Foreign Application Priority Data

Jul. 12, 2001 (DE) .......................... 101 33 927

(51) Int. Cl.[7] ...................... C07D 333/74; C08G 75/00; H01B 1/06

(52) U.S. Cl. ................ 549/43; 528/377; 252/511
(58) Field of Search .................... 549/43; 528/377; 252/511

(56) References Cited

U.S. PATENT DOCUMENTS

| 6,001,867 A | * | 12/1999 | Wrobel et al. ............ 514/414 |
| 6,040,459 A | * | 3/2000 | Yuan et al. .................. 549/43 |
| 6,423,870 B1 | * | 7/2002 | Langlois et al. ........... 564/219 |
| 6,429,312 B2 | * | 8/2002 | Yuan et al. .................. 544/295 |
| 6,555,555 B1 | * | 4/2003 | Konishi et al. ............ 514/324 |
| 6,559,177 B2 | * | 5/2003 | Miller et al. ................ 514/443 |

* cited by examiner

*Primary Examiner*—Deborah C. Lambkin
(74) *Attorney, Agent, or Firm*—Diderico van Eyl; Godfried R. Akorli

(57) ABSTRACT

The invention relates to substituted or unsubstituted benzodioxinothiophenes, their preparation and their use for preparing electrically conductive oligomers or polymers, also oligomers or polymers comprising these thiophene derivatives as repeating unit.

16 Claims, No Drawings

BENZODIOXINOTHIOPHENES, THEIR PREPARATION AND USE

BACKGROUND

The invention relates to substituted or unsubstituted benzo-dioxinothiophenes, hereinafter referred to as 3,4-(1',2'-benzo-dioxy)thiophene, a process for preparing it and its use for preparing electrically conductive oligomers or polymers. The invention further relates to oligomers or polymers which comprise these compounds as repeating unit.

Conductive organic polymers have a wide range of applications. An example which may be mentioned is their use for producing polymer batteries, diodes or transistors or solar cells. As conductive organic polymers, use is made of, for example, systems based on polyacetylene, poly(p-phenylene), polythiophene or polypyrrole.

There are some electrically conductive oligomers and polymers which can be prepared from thiophene derivatives. Previously known electrically conductive oligomers and polymers prepared from thiophene derivatives have aliphatic substituents. A particular example is provided by polymers based on 2,3-dihydrothieno[3,4-b][1,4]dioxin, which is also referred to as 3,4-ethylenedioxythiophene in the literature and is commercially available under the name BAYTRON® M from BAYER AG.

To be able to match the polymer properties to the respective requirements in a targeted way, it is necessary to have many suitable monomer building blocks available. It is therefore an object of the present invention to provide new thiophene derivatives and to find ways of preparing them.

SUMMARY

The invention relates to a compound of the Formula (I):

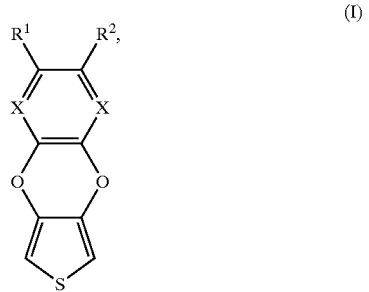

in which $R^1$ and $R^2$ are each, independently of one another, H, $C_1$–$C_{20}$-alkyl, $C_6$–$C_{10}$-aryl, $C_7$–$C_{12}$-aralkyl, $C_1$–$C_{18}$-alkoxy, $C_2$–$C_{18}$-hydroxyalkylenoxy, $C_2$–$C_{36}$-alkoxyalkylenoxy, hydroxyethyl, formyl, $C_2$–$C_{18}$-acyl, nitro, halogen, sulfo (—$SO_3H$), cyano (—CN), carboxy (—COOH), $C_1$-$C_{18}$-alkoxy-carbonyl or trifluoromethyl, or together with the aromatic ring to which they are bound form a fused aromatic ring system, and X is N or C—H.

The invention also relates to a process for preparing a compound of the Formula (I) that involves reacting a 3,4-dialkoxythiophene with a substituted or unsubstituted 1,2-dihydroxybenzene, and thereby making the compound of Formula (I).

The invention also relates to a process for making an electrically conductive polymer comprising polymerizing a compound of the Formula (I).

And the invention relates to an electrically conductive polymer comprising at least one repeating compound of the Formula (I).

The invention is further described in the following illustrative examples in which all parts and percentages are by weight unless otherwise indicated.

DESCRIPTION

New thiophene derivatives have now been able to be prepared. These are substituted or unsubstituted 3,4-(1',2'-benzodioxy)thiophene, which term includes compounds containing a diazabenzo radical. The compounds can bear a wide variety of different substituents which influence the electronic structure in a targeted manner, so that they are particularly interesting and versatile as monomers for preparing conductive polymers.

The invention provides compounds of the Formula (I):

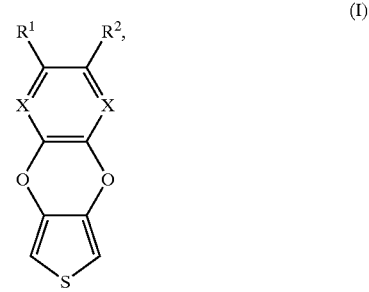

in which $R^1$ and $R^2$ are each, independently of one another, H, $C_1$–$C_{20}$-alkyl, $C_6$–$C_{10}$-aryl, $C_7$–$C_{12}$-aralkyl, $C_1$–$C_{18}$-alkoxy, $C_2$–$C_{18}$-hydroxyalkylenoxy, $C_2$–$C_{36}$-alkoxyalkylenoxy, hydroxyethyl, formyl, $C_2$–$C_{18}$-acyl, nitro, halogen, sulfo (—$SO_3H$), cyano (—CN), carboxy (—COOH), $C_1$-$C_{18}$-alkoxycarbonyl or trifluoromethyl, or together with the aromatic ring to which they are bound form a fused aromatic ring system, and X is N or C—H.

Preference is given to $R^1$ and $R^2$ each being, independently of one another, H, $C_1$–$C_{16}$-alkyl, $C_6$–$C_{10}$-aryl, $C_1$–$C_{18}$-alkoxy, $C_2$–$C_4$-acyl, nitro, halogen, e.g., fluorine, chlorine or bromine, or $C_2$–$C_{36}$-alkoxy-alkylenoxy, particularly preferably H, methyl, butyl, phenyl, acetyl (—CO—$CH_3$), methoxy, methoxyethoxy ($H_3C$—O—$CH_2$—$CH_2$—O—), nitro or chlorine. Very particular preference is given to at least one of the radicals $R^1$ and $R^2$ being hydrogen.

X is preferably C—H.

The compounds of the Formula (I) represent a valuable supplement to the known thiophene derivatives having aliphatic substituents since they are suitable for preparing conductive polymers having particularly favorable properties, in particular a high conductivity. Such polymers can be used, for example, as electrodes.

Compounds of the Formula (I) in which X is C—H can be prepared by, for example, reacting 3,4-dialkoxythiophene, preferably the known 3,4-dimethoxythiophene, with substituted or unsubstituted 1,2-dihydroxy-benzenes.

This reaction can take place, for example, at atmospheric pressure in an aromatic solvent such as xylene or toluene at from about 100 to about 160° C., preferably reflux temperature, in the presence of an acid catalyst, e.g., sulfuric acid or p-toluenesulfonic acid.

Compounds of the Formula (I) in which X is N can be prepared by, for example, reacting a known 3,4-dihydroxythiophenedicarboxylic ester with a substituted or unsubstituted 2,3-dihalo-1,4-diazabenzene and subsequently saponifying and decarboxylating the product of this reaction.

The compounds of the Formula (I) can be used for preparing electrically conductive polymers. Here, it is possible to use either one compound of the Formula (I) as monomer or a mixture of various compounds which come under the definition of Formula (I). It is also possible to add further thiophene derivatives, in particular the known 3,4-ethylenedioxy-thiophene, as monomers in addition to one or more compounds of the Formula (I).

The polymerization is carried out in accordance with polymerization procedures for known thiophene derivatives. It can be carried out, for example, oxidatively using oxidants such as iron(III) chloride or other iron(III) salts, $H_2O_2$, sodium or potassium peroxodisulfate, potassium dichromate, potassium permanganate or electrochemically.

The invention further provides for the use of compounds of the Formula (I) for preparing electrically conductive polymers and provides electrically conductive polymers which are prepared by polymerization of a compound of the Formula (I) and therefore comprise at least one compound of the Formula (I) as repeating units.

The invention is further described in the following illustrative examples in which all parts and percentages are by weight unless otherwise indicated.

EXAMPLES

Example 1

45 g of 3,4-dimethoxythiophene (0.31 mol), 33 g of catechol (0.3 mol), 60 ml of xylene, 1.5 g of p-toluenesulfonic acid and 0.6 g of triphenylphosphine were heated to boiling (145° C.) under protective gas for 24 hours. Methanol formed was distilled off during this time.

To monitor the course of the reaction, samples were taken at intervals and analyzed by HPLC. The reaction was stopped as soon as all of the 3,4-dimethoxythiophene used had reacted.

After cooling, the mixture was extracted four times with 50 ml each time of cyclohexane. The first cyclohexane extract was deep reddish brown, and the following extracts became increasingly light in color and contained increasingly pure product. The extracts were combined and allowed to stand overnight, resulting in precipitation of a dark reddish brown oil which was separated off.

The oil was evaporated on a rotary evaporator and freed of xylene and taken up in 200 ml of cyclohexane.

The combined cyclohexane solutions were admixed with 0.4 g of activated carbon, heated to 70° C. and filtered. The clarified solution was evaporated to dryness on a rotary evaporator (70° C., 25 mbar).

This gave 14.8 g of slightly yellowish product which had a melting point of 60° C. and, according to GC-MS analysis, contained 99% of benzothienodioxin (3,4-(1',2'-benzodioxy)thiophene). MS: m/e=190 (100%).

The product was purified further by chromatography (eluant: cyclohexane, on silica gel as stationary phase). This gave a pure white, crystalline product which melts at 72° C.

In the infrared spectrum (KBr pellet), the product absorbs strongly at 1509, 1493, 1281, 766 and 742 cm$^{-1}$.

1H—NMR (CDCl$_3$): 6.39 ppm (s, 2H), 6.88 ppm (s, 4H).

The compound can be polymerized, for example electrochemically, to form an electrically conductive film or firstly polymerized by oxidation using iron(III) tosylate in ethanol and then processed from chloroform to give an electrically conductive film.

Example 2

12.5 g of 3,4-di-n-propyloxythiophene, 20.7 g of 4-tert-butylcatechol and 1.2 g of p-toluenesulfonic acid monohydrate were refluxed in 90 ml of toluene under a protective gas atmosphere for 3 hours. A mixture of toluene and n-propanol which had been formed was subsequently distilled off. The amount of solvent distilled off was replaced in portions firstly by toluene, then by xylene. Distillation was continued for a total of 12 hours. The course of the reaction was monitored by means of thin-layer chromatography.

After the reaction was complete, the mixture was cooled and the dark solution obtained was washed three times with water. The solvent was distilled off under reduced pressure on a rotary evaporator and the black residue was purified by preparative column chromatography (on SiO$_2$ (silica gel) as stationary phase using toluene as eluant). This gave 16.6 g of a dark red oil which, according to 1H-NMR, contained 65% of 3,4-(4'-tert-butylbenzo-1',2'-dioxy)thiophene.

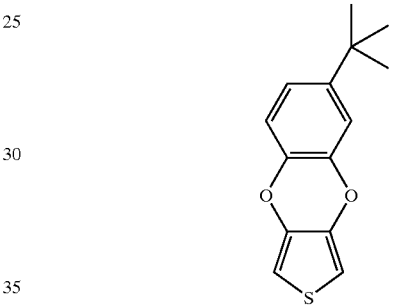

1H—NMR (CDCl$_3$): 1.28 ppm (9H, s), 6.40 ppm (2H, s), 6.8–6.95 ppm (2H, aromat. AB system), 6.94 ppm (1H, s).

Example 3

Polymerization of 3,4-(1',2'-benzodioxy)thiophene 5.0 g of iron(III) p-toluenesulfonate were dissolved in 10.4 g of ethanol. 0.58 g of 3,4-(1',2'-benzodioxy)thiophene were added to the solution. The mixture was stirred at room temperature for 1 hour and the solution was subsequently poured onto a glass plate or another substrate and the layer was spread to form a thin film, for example by spin coating. The film was subsequently dried at 75° C. for 1 hour.

This gave a dark blue film having a slight violet tinge. The film was somewhat darker than a comparative film which had been obtained from 3,4-ethylenedioxythiophene under identical conditions.

The film displayed electrical conductivity.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound of the Formula (I):

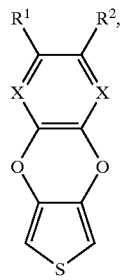

(I)

wherein $R^1$ and $R^2$ are each, independently of one another, H, $C_1$–$C_{20}$-alkyl, $C_6$–$C_{10}$-aryl, $C_7$–$C_{12}$-aralkyl, $C_1$–$C_{18}$-alkoxy, $C_2$–$C_{18}$-hydroxy-alkylenoxy, $C_2$–$C_{36}$-alkoxyalkylenoxy, hydroxyethyl, formyl, $C_2$–$C_{18}$-acyl, nitro, halogen, sulfo (—$SO_3H$), cyano (—CN), carboxy (—COOH), $C_1$–$C_{18}$-alkoxycarbonyl or trifluoromethyl, or together with the aromatic ring to which they are bound form a fused aromatic ring system, and X is C—H.

2. The compound according to claim 1, wherein $R^1$ and $R^2$ are each, independently of one another, H, $C_1$–$C_{16}$-alkyl, $C_6$–$C_{10}$-aryl, $C_1$–$C_{18}$-alkoxy, $C_2$–$C_4$-acyl, nitro, halogen or $C_2$–$C_{36}$-alkoxyalkylenoxy.

3. The compound according to claim 2, wherein $R^1$ and $R^2$ are each, independently of one another, H, methyl, butyl, phenyl, acetyl (—CO—$CH_3$), methoxy, methoxyethoxy, nitro or chlorine.

4. The compound according to claim 1, wherein at least one of the radicals $R^1$ and $R^2$ is H.

5. A process for preparing a compound of the formula (I):

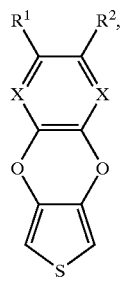

(I)

wherein $R^1$ and $R^2$ are each, independently of one another, H, $C_1$–$C_{20}$-alkyl, $C_6$–$C_{10}$-aryl, $C_7$–$C_{12}$-aralkyl, $C_1$–$C_{18}$-alkoxy, $C_2$–$C_{18}$-hydroxy-alkylenoxy, $C_2$–$C_{36}$-alkoxyalkylenoxy, hydroxyethyl, formyl, $C_2$–$C_{18}$-acyl, nitro, halogen, sulfo (—$SO_3H$), cyano (—CN), carboxy (—COOH), $C_1$–$C_{18}$-alkoxycarbonyl or trifluoromethyl, or together with the aromatic ring to which they are bound form a fused aromatic ring system, and X is C—H, the process comprising reacting a 3,4-dialkoxythiophene with a substituted or unsubstituted 1,2-dihydroxybenzene, and thereby making the compound of Formula (I).

6. The process of claim 5, wherein $R^1$ and $R^2$ are each, independently of one another, H, $C_1$–$C_{16}$-alkyl, $C_6$–$C_{10}$-aryl, $C_1$–$C_{18}$-alkoxy, $C_2$–$C_4$-acyl, nitro, halogen or $C_2$–$C_{36}$-alkoxyalkylenoxy.

7. The process according to claim 5, wherein $R^1$ and $R^2$ are each, independently of one another, H, methyl, butyl, phenyl, acetyl (—CO—$CH_3$), methoxy, methoxyethoxy, nitro or chlorine.

8. The process according to claim 5, wherein at least one of the radicals $R^1$ and $R^2$ is H.

9. A process for making an electrically conductive polymer comprising polymerizing a compound of the Formula (I):

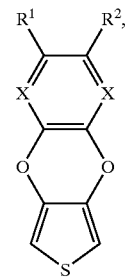

(I)

wherein $R^1$ and $R^2$ are each, independently of one another, H, $C_1$–$C_{20}$-alkyl, $C_6$–$C_{10}$-aryl, $C_7$–$C_{12}$-aralkyl, $C_1$–$C_{18}$-alkoxy, $C_2$–$C_{18}$-hydroxyalkylenoxy, $C_2$–$C_{36}$-alkoxyalkylenoxy, hydroxyethyl, formyl, $C_2$–$C_{18}$-acyl, nitro, halogen, sulfo (—$SO_3H$), cyano (—CN), carboxy (—COOH), $C_1$–$C_{18}$-alkoxycarbonyl or trifluoromethyl, or together with the aromatic ring to which they are bound form a fused aromatic ring system, and X is C—H, and thereby forming the electronically conductive polymer.

10. The process according to claim 9, wherein $R^1$ and $R^2$ are each, independently of one another, H, $C_1$–$C_{16}$-alkyl, $C_6$–$C_{10}$-aryl, $C_1$–$C_{18}$-alkoxy, $C_2$–$C_4$-acyl, nitro, halogen or $C_2$–$C_{36}$-alkoxyalkylenoxy.

11. The process according to claim 9, wherein $R^1$ and $R^2$ are each, independently of one another, H, methyl, butyl, phenyl, acetyl (—CO—$CH_3$), methoxy, methoxyethoxy, nitro or chlorine.

12. The process according to claim 9, wherein at least one of the radicals $R^1$ and $R^2$ is H.

13. An electrically conductive polymer comprising at least one repeating compound of the Formula (I):

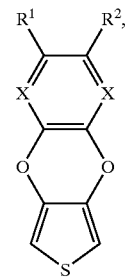

(I)

wherein $R^1$ and $R^2$ are each, independently of one another, H, $C_1$–$C_{20}$-alkyl, $C_6$–$C_{10}$-aryl, $C_7$–$C_{12}$-aralkyl, $C_1$–$C_{18}$-alkoxy, $C_2$–$C_{18}$-hydroxyalkylenoxy, $C_2$–$C_{36}$-alkoxyalkylenoxy, hydroxyethyl, formyl, $C_2$–$C_{18}$-acyl, nitro, halogen, sulfo (—$SO_3H$), cyano (—CN), carboxy (—COOH), $C_1$–$C_{18}$-alkoxycarbonyl or trifluoromethyl, or together with the aromatic ring to which they are bound form a fused aromatic ring system, and X is C—H.

14. The polymer according to claim 13, wherein $R^1$ and $R^2$ are each, independently of one another, H, $C_1$–$C_{16}$-alkyl, $C_6$–$C_{10}$-aryl, $C_1$–$C_{18}$-alkoxy, $C_2$–$C_4$-acyl, nitro, halogen or $C_2$–$C_{36}$-alkoxyalkylenoxy.

15. The polymer according to claim 13, wherein $R^1$ and $R^2$ are each, independently of one another, H, methyl, butyl, phenyl, acetyl (—CO—$CH_3$), methoxy, methoxyethoxy, nitro or chlorine.

16. The polymer according to claim 13, wherein at least one of the radicals $R^1$ and $R^2$ is H.

* * * * *